United States Patent
Fripp (10) Patent No.: US 6,372,486 B1
(45) Date of Patent: Apr. 16, 2002

(54) THERMO CYCLER

(75) Inventor: David M. Fripp, Ashford (GB)

(73) Assignee: Hybaid Limited, Middlesex (GB)

( * ) Notice: Subject to any disclaimer, the term of this patent is extended or adjusted under 35 U.S.C. 154(b) by 0 days.

(21) Appl. No.: 09/451,233

(22) Filed: Nov. 29, 1999

(51) Int. Cl.$^7$ ................................................. C12M 1/38
(52) U.S. Cl. ............................... 435/303.1; 435/286.1; 435/809; 435/305.2; 62/3.3; 165/206
(58) Field of Search ........................... 435/91.2, 305.2, 435/287.2, 286.1, 303.1, 809; 165/206; 62/159, 160, 3.3, 3.2

(56) References Cited

U.S. PATENT DOCUMENTS

| | | | |
|---|---|---|---|
| 4,679,615 A | | 7/1987 | Livne |
| 4,860,748 A | * | 8/1989 | Chiurco et al. |
| 5,066,377 A | | 11/1991 | Rosenbaum et al. |
| 5,224,536 A | | 7/1993 | Eigen et al. |
| 5,280,094 A | | 1/1994 | Mulhall |
| 5,430,957 A | | 7/1995 | Eigen et al. |
| 5,441,576 A | * | 8/1995 | Bierschenk et al. |
| 5,525,300 A | | 6/1996 | Danssaert et al. |
| 5,576,512 A | * | 11/1996 | Doke |
| 5,601,141 A | * | 2/1997 | Gordon et al. |
| 5,716,842 A | | 2/1998 | Baier et al. |
| 5,802,856 A | * | 9/1998 | Schaper et al. |
| 5,819,842 A | * | 10/1998 | Potter et al. |
| 6,086,831 A | * | 7/2000 | Harness et al. |
| 6,106,784 A | * | 8/2000 | Lund et al. |

FOREIGN PATENT DOCUMENTS

| | | |
|---|---|---|
| DE | 1 900 279 | 9/1969 |
| DE | 7113471 | 7/1971 |
| DE | 31 22 008 A1 | 3/1982 |
| DE | 35 25 860 A1 | 1/1987 |
| DE | 276 547 A1 | 2/1990 |
| DE | 44 06 107 C1 | 5/1995 |
| DE | 196 46 115 A1 | 5/1998 |
| EP | 0 504 435 A1 | 9/1992 |
| WO | WO 89/12502 | 12/1989 |
| WO | WO 91/06369 | 5/1991 |

* cited by examiner

Primary Examiner—William H. Beisner
(74) Attorney, Agent, or Firm—Craig A. Fieschko, Esq.; DeWitt Ross & Stevens S.C.

(57) ABSTRACT

A thermal cycler for controlled heating and cooling of biological samples uses eight Thermoelectric Coolers (TECs), positioned between a metal sample plate and a heat sink (2). By altering the polarity of the applied current through the TEC, the temperature of the sample plate can be raised or lowered. When uniform heating and cooling of the sample plate is required, all eight TECs are connected in series and in the same polarity. To produce temperature gradients across the sample plate, the relative polarity of individual TECs is changed or they are bypassed altogether.

19 Claims, 8 Drawing Sheets

THERMO CYCLER

FIELD OF THE INVENTION

The present invention relates to a thermal cycler for use in carrying out controlled heating and cooling of biological samples, for example DNA strands.

BACKGROUND OF THE INVENTION

Traditionally, scientists have used the technique of the Polymerase Chain Reaction (PCR) to synthesize defined sequences of DNA. This generally involves a three step procedure: separation of the DNA to be amplified (template DNA); annealing of short complimentary DNA sequences (primers) to the template DNA and finally the addition of deoxynucleotides to the primer strands in order to copy the template DNA. This is usually performed in a thermal cycling machine where a cycle of three different temperatures is repeated approximately 25–35 times. Template DNA separation and synthesis steps occur at defined temperatures. However, the temperature at which the primer binds to the DNA, may need optimizing in order for this step to occur efficiently and achieve desirable PCR results. Primer annealing optimization experiments usually involve setting up a number of different experiments where only the primer annealing temperature is varied. The experiment may need to be performed 3 or 4 times in order to determine the optimum binding temperature. These experiments would have to be repeated each time a new set of primers was required for different PCRs. The development of a temperature gradient block enables the scientists to determine the optimum binding temperatures of several primer sets in a single experiment.

However, prior art derives which produce a thermal gradient have been relatively complex and expensive.

SUMMARY OF THE INVENTION

The present invention seeks to provide an improved thermal cycler.

According to an aspect of the present invention, there is provided a thermal cycler including a sample plate able to hold a plurality of samples, a plurality of heating and cooling elements located along the sampling plate, supply means operable to provide a current to the heating and cooling elements, and switching means able to switch current individually through each heating or cooling element or each of a plurality of sets of heating or cooling elements.

The temperature gradient block can achieve a set of discrete temperatures simultaneously, thereby decreasing the number of optimization experiments the scientist needs to perform and therefore the workload.

DESCRIPTION OF THE DRAWINGS

An embodiment of the present invention is described below, by way of example only, with reference to the accompanying drawings, in which.

DESCRIPTION OF THE PREFERRED EMBODIMENT

Figure 1:
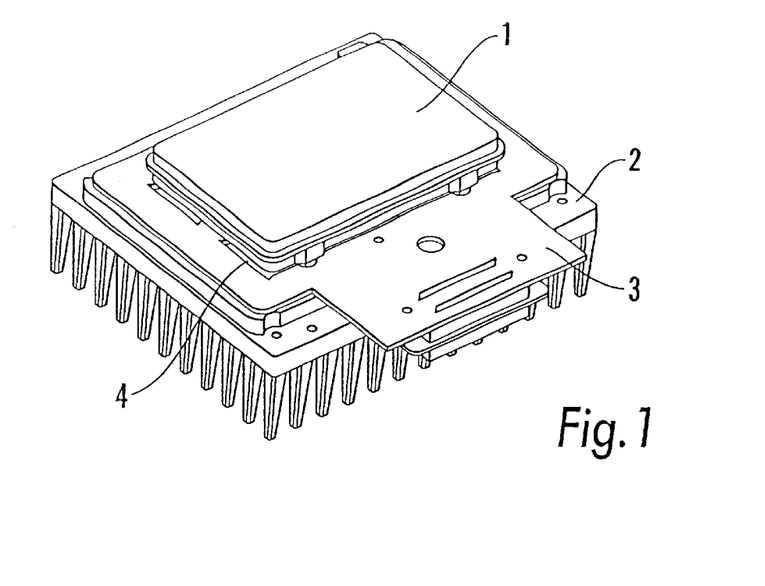
FIG. 1 is a perspective view of an embodiment of heating and cooling block of a thermal cycler.

Controlled heating and cooling of biological samples is preferably achieved by using Thermoelectric Coolers (TECs). This embodiment uses 8 such devices, positioned between a metal sample plate and a heat sink 2 arranged a shown in FIG. 1.

A TEC will generate a temperature differential across its surfaces when a current is applied. By altering the polarity of the applied current, the temperature of the sample plate can be raised or lowered, as is known in the art. When uniform heating and cooling of the sample plate is required, all 8 TECs are connected in series and in the same polarity. To produce temperature gradients across the sample plate, the relative polarity of individual TECs is changed or they are bypassed altogether.

Figure 2:
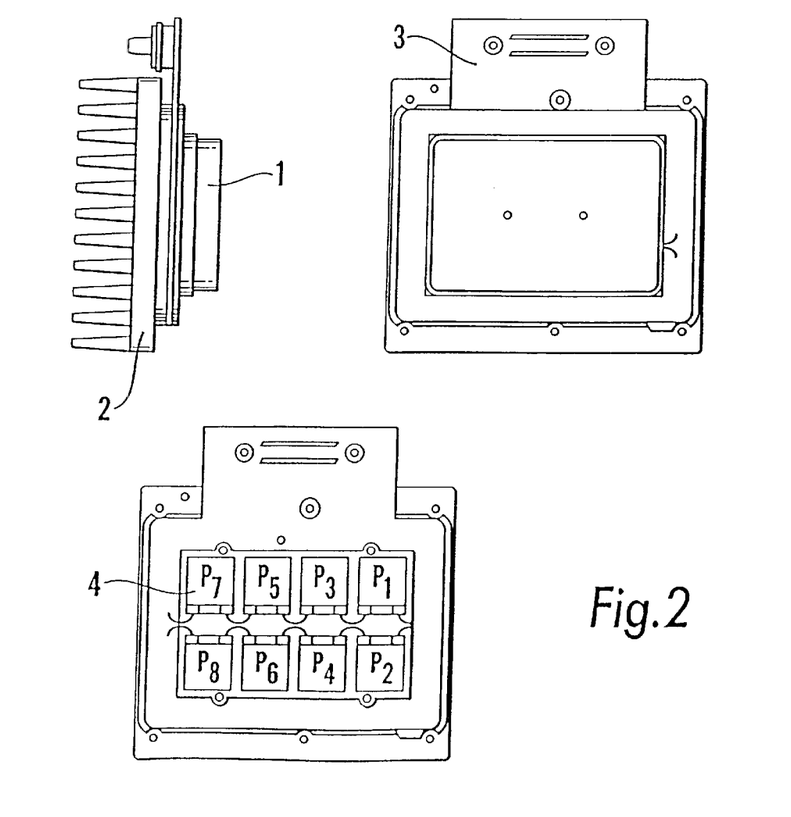
FIG. 2 shows different elevational views of the block of FIG. 1 with the sample plate attached and removed to reveal a plurality of heating and cooling elements.

Referring to FIG. 2, a circuit board 3 (described in greater detail below) is located on the heat sink, and in this example, eight TECs 4 are located over the circuit board 3. The sample plate 1 is of conventional form and typically is able to hold many samples in an organized array.

Referring to FIGS. 3 to 8, the circuit used to deliver current to the TECs 4 is shown in various operating states. The specific component types mentioned below are given by way of example only. The skilled person will readily be able to find alternatives.

Figure 3:
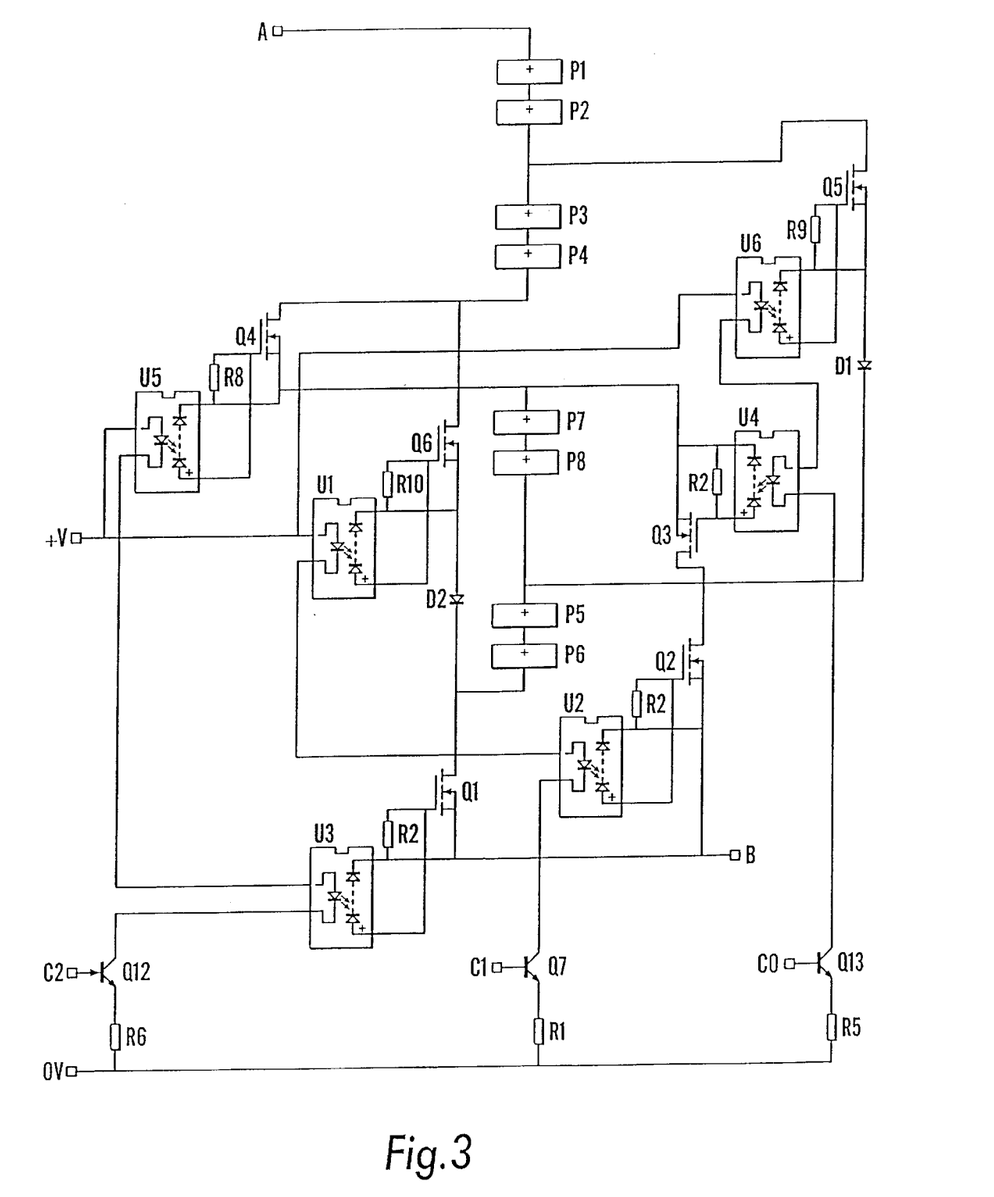
FIGS. 3 to 8 show an example of circuit diagram for driving the heating and cooling elements of FIG. 2 in different manners.

Current flow through the TECs is switched by means of MOSFETs (International Rectifier IRLI3705N) shown in FIG. 3 as Q1–Q6. The design uses International Rectifier PVI5100 Photovoltaic Isolators, U1–U6, to provide a gate drive voltage for each MOSFET which is isolated from the control interface.

Figure 4:
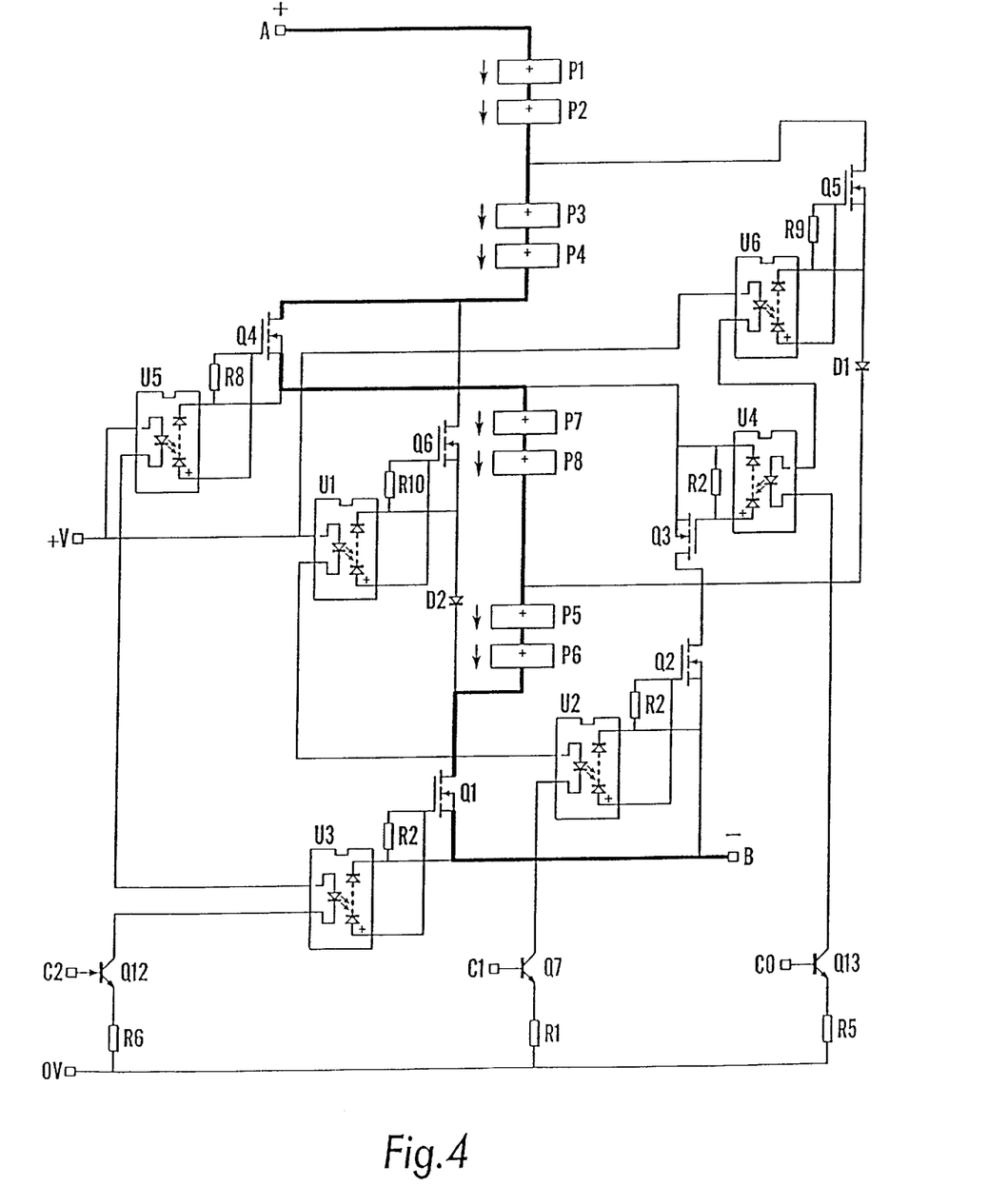
Figure 5:
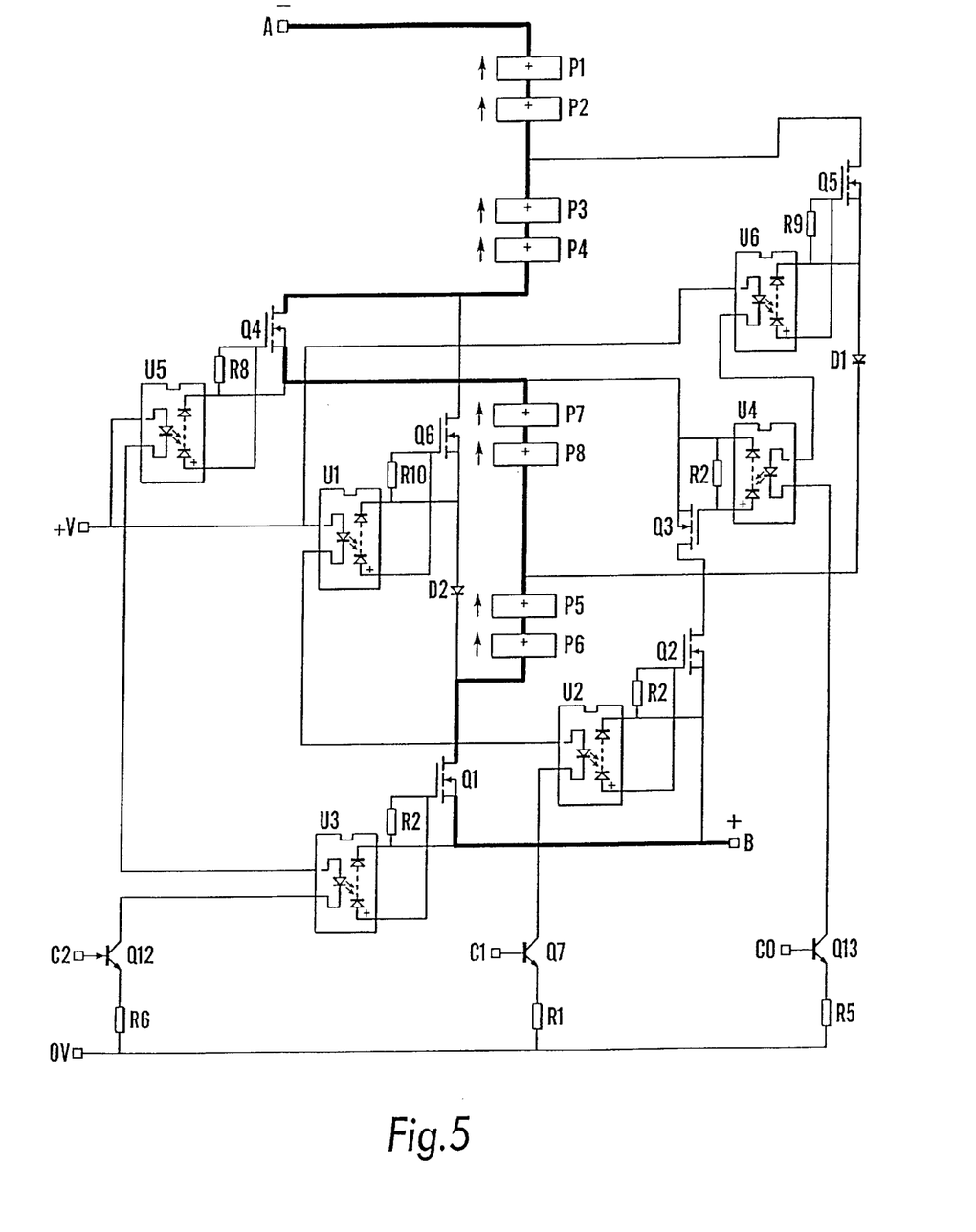

To achieve uniform heating and cooling, control signal C2 is set to logic to provide base current for Q12 which activates U3 and U5 and enables MOSFETs Q1 and Q4. With a positive voltage on A with respect to B, current flow in the TECs is as shown in FIG. 4, resulting in uniform cooling of the sample plate 1. With a negative voltage on A with respect to B, current flow in the TECs is as shown in FIG. 5, resulting in uniform heating of the sample plate. In this case, current flows through the parasitic diodes in Q1 and Q4.

Figure 6:
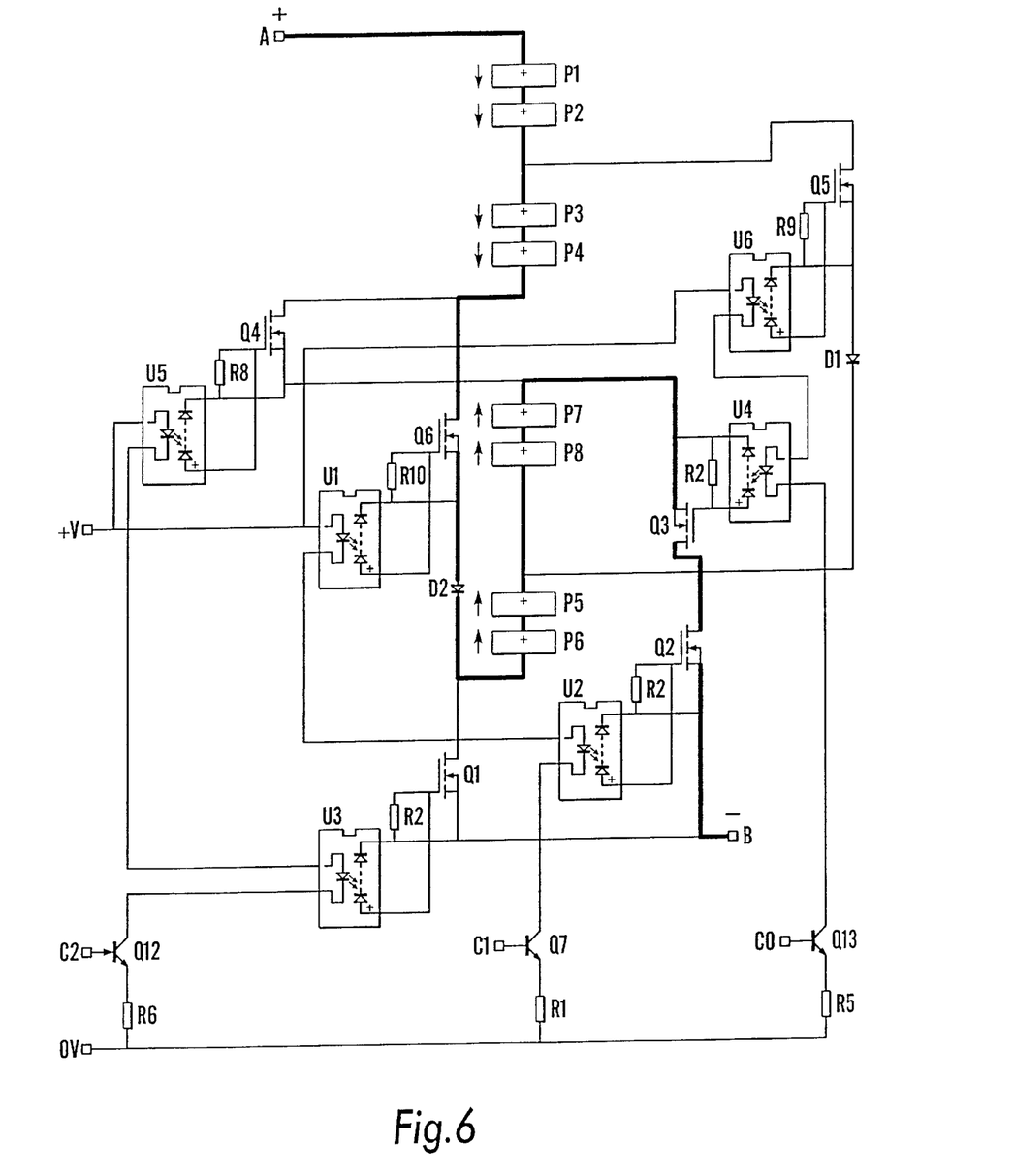

To achieve a temperature gradient across the sample plate 1, control signal C1 is set to logic '1' to provide base current for Q7 which activates U2 and U1 and enables MOSFETs Q2 and Q6. With a positive voltage on A with respect to B, current flow in each of the TECs is as shown in FIG. 6, resulting in a cooling effect in TECs P1, P2, P3 and P4 and a heating effect in TECs P5, P6, P7 and P8. Note that in this case, current flows through the parasitic diode in Q3.

Figure 7:
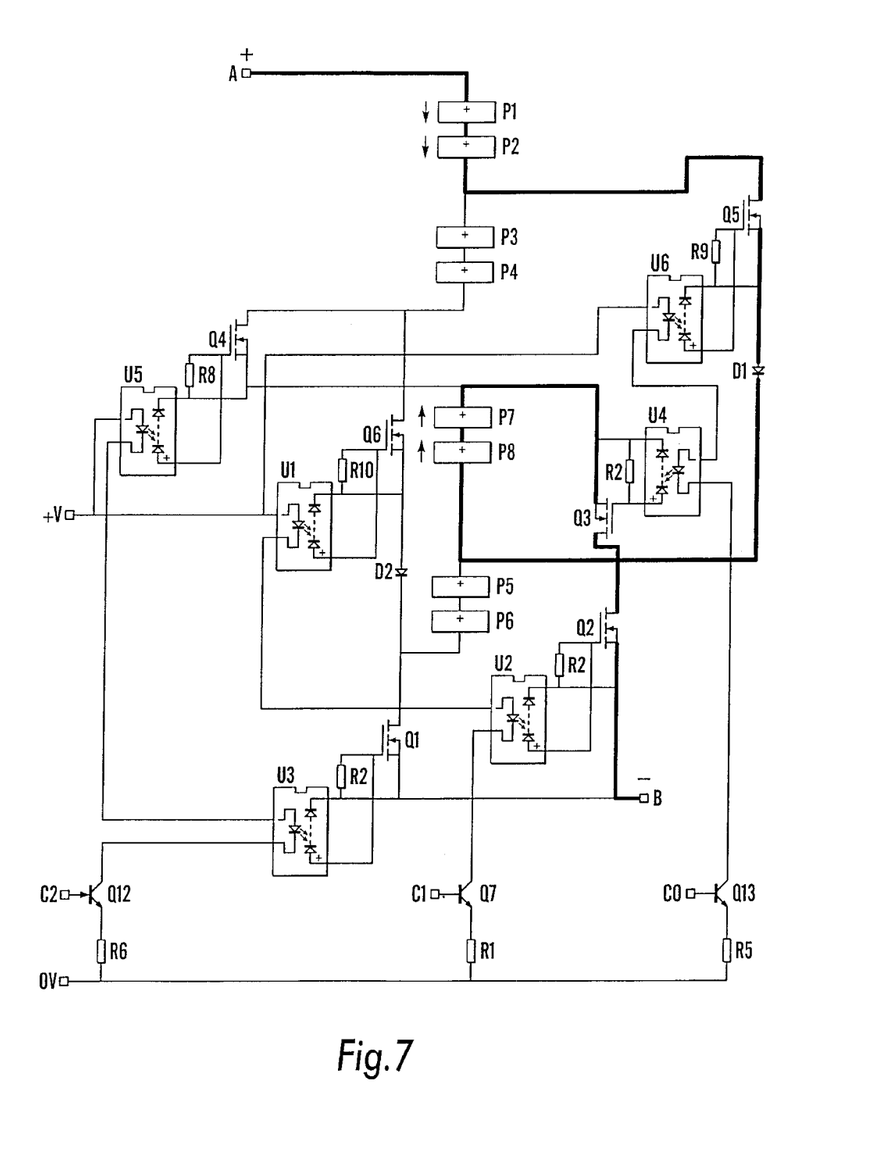

In order to obtain a more linear gradient across the sample plate 1, less heating/cooling is required from the inner TECs P3, P4, P5 and P6. This is achieved by bypassing these TECs while keeping TECs P1, P2, P7, and P8 in a 'gradient' configuration. Control signals C1 and C0 are set to logic '1' to provide base current for Q7 and Q13 which activates U1, U2, U4 and U6, and enables MOSFETs Q2, Q3, Q5 and Q6. With a positive voltage on A with respect to B, current flow in the TECs is as shown in FIG. 7, resulting in a cooling effect in TECs P1 and P2 and a heating effect in TECs P7 and P8. Note that in this case current flows through the parasitic diode in Q3.

Figure 8:
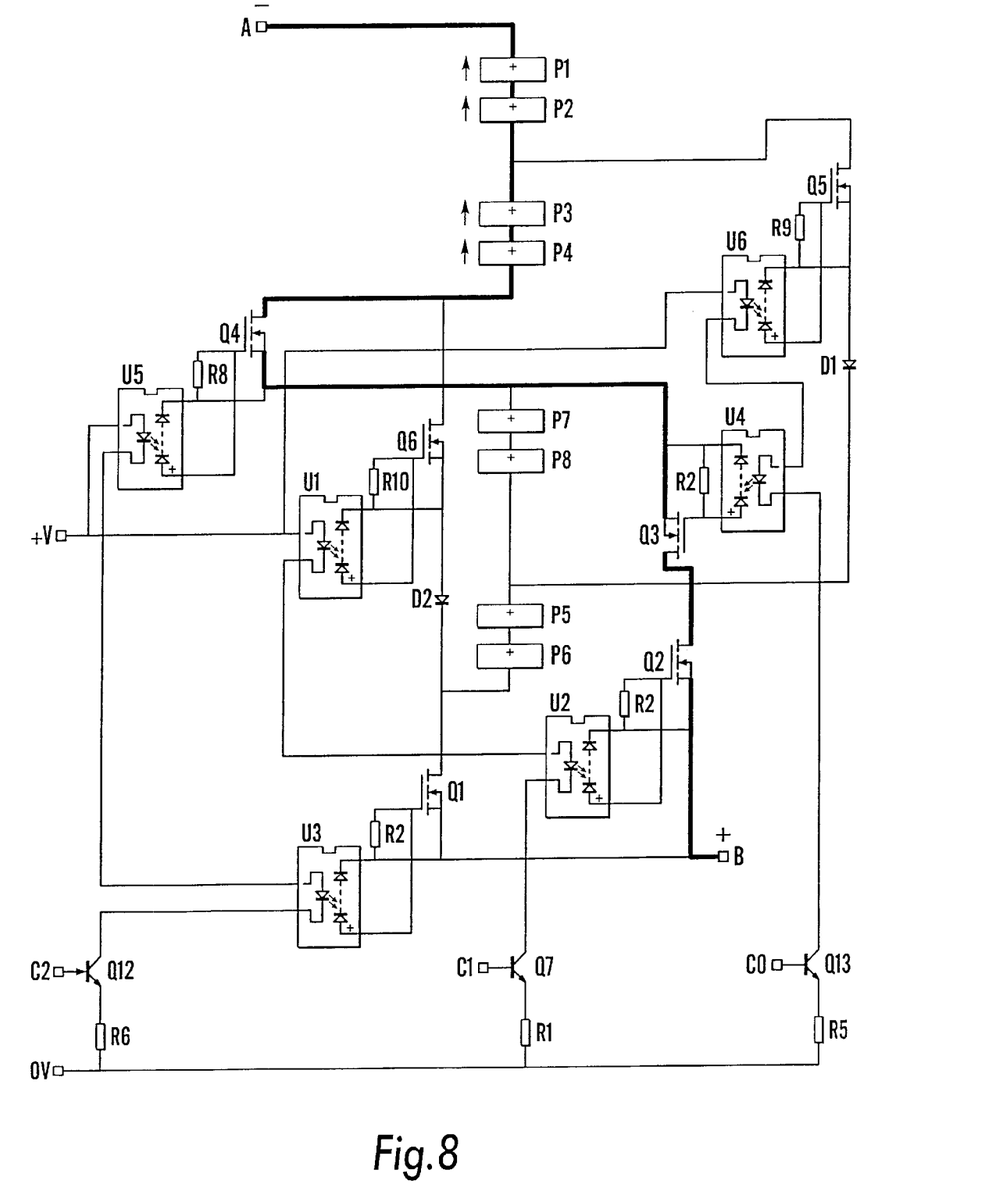

By setting control signals C2 and C0 to logic '1' base current is provided for Q12 and Q13 which activates U3, U4, U5 and U6 and enables MOSFETs Q1, Q3, Q4 and Q5. With a negative voltage on A with respect to B, current flow in the TECs as shown in FIG. 8, resulting in a heating effect in TECs P1, P2, P3 and P4 only. This mode of operation is used to help re-establish temperature uniformity across the sample plate. Note that in this case current flows through the parasitic diode in Q2.

It will be apparent that the current through the inner TECs P3, P4, P7 and P8 can be switched intermittently to produce any desired temperature gradient, as can be done with the outer TECs P1, P2, P5 and P6. The duty cycles suitable for the various TECs can be determined by experimentation.

Figure 9:
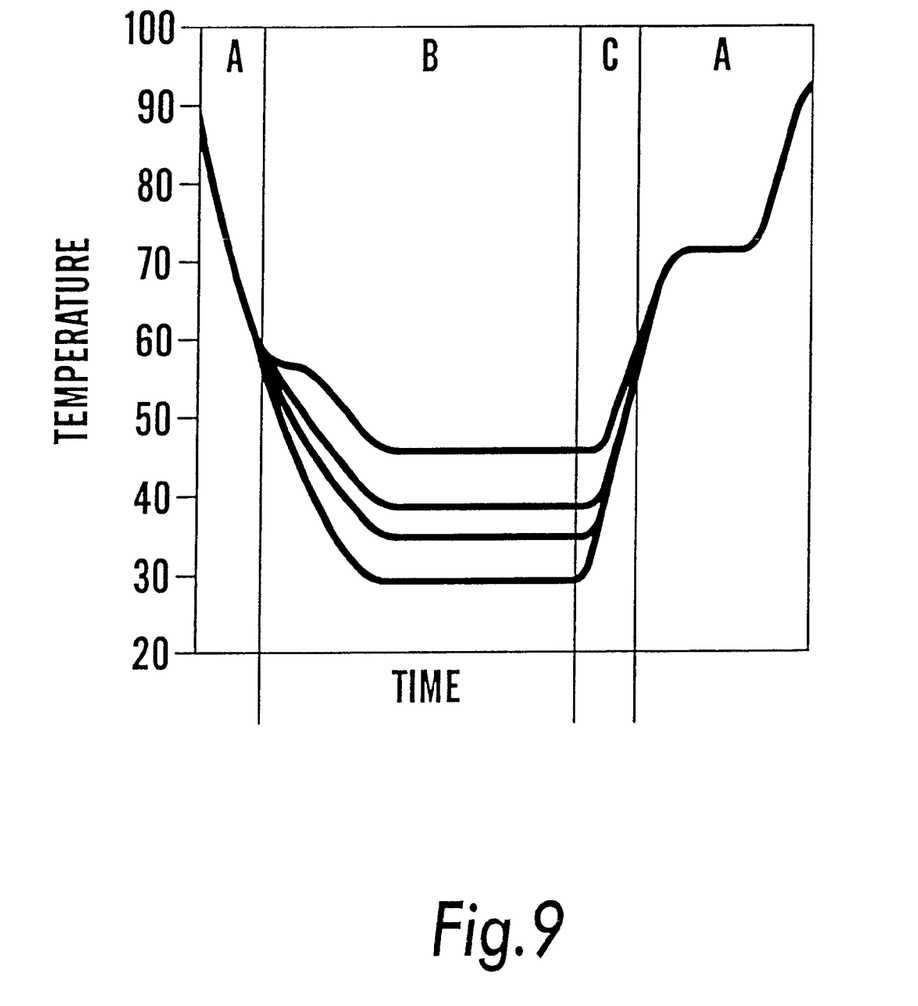
FIG. 9 is a graph showing the time/temperature characteristics of the thermal cycler of FIG. 1.

FIG. 9 shows a typical temperature/time characteristic obtained using this technique. Each line on the graph represents the temperature of particular locations on a line running from left to right across the sample plate 1.

Zone A represents uniform cooling or heating. Current flow through the TECs is as shown in FIG. 4 (cooling) and FIG. 5 (heating).

Zone B represents operation in gradient mode. In this mode, uniform heating and cooling is used in combination with the gradient operation, represented in FIGS. 6 and 7, to achieve the desired temperature set-point and the desired temperature gradient.

Zone C represents the recovery from gradient mode. Temperature uniformity across the sample plate is re-established by a combination of uniform heating and partial heating represented in FIG. 8.

It will be apparent that the pairing of TECs for the purposes of heating/cooling is merely exemplary.

A description of the preferred method of operation of the system, advantageously provided in software, is given below.

The eight Peltier Thermo Electric Coolers (TECs) are wired in four pairs of two. Three control signals are used to switch the arrangement of Field Effect Transistors (FETs) Q1 to Q4, which in turn are used to switch pairs of TECs in or out of the circuit. The four pairs of TECs can be driven in the following modes:

1. Common mode, where all four pairs are used for heating or cooling.
2. Differential mode, where two pairs at one end are used for heating and two pairs at the opposite end are used for cooling. This mode is used during a gradient step.
3. Half Differential mode, where the two outer pairs only are driven. This mode is used to improve linearity across the block during a gradient step.
4. Start Gradient mode, where the two pairs used at the cooler end of the block are cooled, and the other two pairs are not driven. This mode is used when starting a gradient step.
5. Stop Gradient mode, where the two pairs at the cooler end of the block are heated, and the other two pairs are not driven. This mode is used when ending a gradient step.

A PID loop controls the temperature of the block, based on measurements taken from a thermistor embedded in one end of the block. Switching the TECs between the various operating modes for a calculated period of time enables the temperature gradient to be accurately controlled.

FET States

The Gradient Temperature Block circuitry gives nine possible FET states. These states are the combination on the three control bits C2, C1 and C0, with the power supply polarity, + or −.

Each of the sixteen combinations are named 0+, 0−, 1+, 1− ... 7+, 7−.

Of these sixteen combinations, only nine are usable because the FETs have diodes allowing reverse current to flow:

| NAME | 1 | 2 | 3 | 4 | STATES |
|------|---|---|---|---|--------|
| Off | — | — | — | — | 0−, 1− |
| Heat | H | H | H | H | 0+, 2+, 4+, 6+ |
| Cool | C | C | C | C | 4− |
| Differential | C | C | H | H | 2− |
| Start Gradient | C | C | — | — | 6− |
| Stop Gradient | H | H | — | — | 1+, 3+, 5+, 7+ |
| Half Differential | C | — | — | H | 3− |
| Cool Ends | C | — | — | C | 5− |
| Not Used (!) | C | c | h | c | 7− |

Column 1 represents the variable (cooler) end of the block, column 4 is the fixed end.
H indicates Heating, C is Cooling and — is no change
Mode 7− is not used because it gives c = 1/3 Cooling and h = 1/3 Heating
Only the states in bold are used in the Express program
State 6− is only on for one time slot, and has a negligible effect. It is thought that this method of starting up a gradient was never fully implemented.

A 50:50 ratio mix of 2− and 3− gives an average as follows:

| 2− | C | C | H | H |
|----|---|---|---|---|
| 3− | C | — | — | H |
| Sum | 2C | C | H | 2H |

This gives a linear slope State 3+ indicates the C2=0, C1=C0=1 and the power supply is in Positive mode. This corresponds to the +ve supply connected to the B terminal on the circuit diagram.

Mode of Operation

A global variable called gradient is set when the temperature gradient needs to be changed. This is calculated from the measured gradient and required gradient.

In Normal mode CurrentDemand(0) is used to set the power supply.

In Gradient mode CurrentDemand(1) is used to set the power supply. This is clipped to 0 or negative values since the Differential, Half Gradient and Reverse Differential FET states only work with one direction of current.

In Normal modes, one time value, called ZoneTime(0), is calculated from the CurrentDemand(0) value.

In Gradient modes, two time values are calculated from the CurrentDemand(1) value. These are called ZoneTime(0) and ZoneTime(1).

ZoneTime(1) is always set to one half of ZoneTime(0).

ZoneTime(0) is the number of time slots out of 190 which the power supply is on.

ZoneTime(1) marks the mid point of ZoneTime(0) so that in increasing gradient mode the FET state can be 50% differential and 50% half differential (ends only).

A finite sate machine called UpdateCurrentDemand is used to control the process—

State 0 initialises variables

State 1 decides on one of three sub-machines:

1. Normal
2. Increase the gradient
3. Decrease the gradient

For an increase or decrease in gradient 256/446 slots are Normal mode and 190 are Gradient mode.

Normal Mode

The process is divided up into 190 timeslots.

The FET state is switched to Normal.

The power supply is on for ZoneTime(0) out 190 slots, then switched off.

Increasing Gradient Mode

The process is divided up into 190+256=446 timeslots.

The FET state is Differential(2−) for half ZoneTime(0), then Half Differential(3−) for another half ZoneTime (0). (This gives a more linear slope than just one of the states on its own).

Then the power supply is switched off until slot 191.

Then the FET state is switched to Normal (4+, 4−) and Gradient mode disabled for 258 slots.

Decreasing Gradient Mode

The process is divided up into 190=266=446 timeslots.

The FET state is Reverse Differential(5+) for ZoneTime (0).

The FET state is then switched to Normal and Gradient mode disabled for 256 slots.

Then the power supply is switched off until slot 191.

Then the FET state is switched to Normal (4+, 4−) and Gradient mode disabled for 256 slots.

For either gradient mode the power supply is on for ZoneTime(0) in gradient mode (if required) out of the first 190 slots, then for another ZoneTime(0) out of the next 256 slots in normal mode.

Summary

In normal (non gradient) mode the power supply is pulse width modulated so that it is on for ZoneTime(0) slots out of 190. The PWM ratio is calculated by the main PID loop.

In gradient mode, when a change of gradient is required, the FET state is adjusted to give the required change, and the gradient PID loop calculates the ZoneTime(0), ZoneTime(1) and required current.

When the 190 slots are completed, the unit is switched into normal mode for 256 slots, so that the overall block temperature can be adjusted. If a change in gradient is not required the unit remains in normal mode.

We claim:

1. A thermal cycler including a sample plate able to hold a plurality of samples, a plurality of heating and cooling elements located along the sampling plate, supply means operable to provide a current to the heating and cooling elements, and switching means able to switch current individually through each heating or cooling element or each of a plurality of sets of heating or cooling elements.

2. A thermal cycler according to claim 1, wherein the switching means is operable selectively to switch the direction of current through the heating and cooling elements.

3. A thermal cycler according to claim 1, wherein the switching means is operable selectively to disconnect the supply means from the heating and cooling elements.

4. A thermal cycler according to claim 1, wherein the switching means is operable to connect at least some of the heating and cooling elements in series with one another.

5. A thermal cycler according to claim 1, wherein the switching means is operable to switch the supply to provide current in a first direction to some of the heating and cooling elements and in a second direction to others of the heating and cooling elements.

6. A thermal cycler according to claim 1, wherein the switching means is operable to switch the supply to provide current intermittently to one or more of the heating and cooling elements.

7. A method of operating a thermal cycler which includes a heat conductive sample plate able to hold a plurality of samples, a plurality of heating and cooling elements located along the sampling plate in heat conductive contact therewith, a common supply means operable to provide a current to the plurality of heating and cooling elements, and switching means able to switch current individually through each heating or cooling element or each of a plurality of sets of heating or cooling elements; comprising the steps of:

switching the direction of current selectively through the heating and cooling elements to produce a plurality of different heating modes along the sample plate and thereby produce uniform temperatures or temperature gradients across the sample plate through heat conduction.

8. A method according to claim 7, wherein a heat gradient is created along the sample plate by heating or cooling the heating and cooling element or elements at one end of the plate and providing substantially no power to the heating and cooling element or elements at the other end of the plate.

9. A method according to claim 8, wherein a heat gradient along the sample plate is removed by heating or cooling the heating and cooling element or elements at one end of the plate and providing substantially no power to the heating and cooling element or elements at the other end of the plate.

10. A method according to claim 7, wherein a heat gradient along the sample plate is removed by heating or cooling the heating and cooling element or elements at one end of the plate and providing substantially no power to the heating and cooling element or elements at the other end of the plate.

11. A method according to claim 7, wherein the switching means is operable in a common mode, a differential mode and/or a half differential mode.

12. A method according to claim 11, wherein control of a temperature gradient across the sample plate is effected by switching of operating mode.

13. A method according to claim 7, wherein a heat gradient created along the sample plate is altered by altering a duty cycle of the switching means.

14. A thermal cycler including:

a. a heat conductive sample plate able to hold a plurality of samples, b. a plurality of heating and cooling elements located along the sampling plate in heat conductive contact therewith, c. a common supply means coupled to provide a current to the plurality of heating and cooling elements, and d. switching means able to switch current individually
 (i) through each heating or cooling element, or
 (ii) through each of a plurality of sets of heating or cooling elements respectively, to produce different heating or cooling effects in individual ones of the heating or cooling elements, or in indidual sets of the heating or cooling elements, and thereby produce umform temperature gradients across the sample plate through heat conduction.

15. The thermal cycler of claim 14 wherein the switching means is operable selectively to switch the direction of current through the heating and cooling elements.

16. The thermal cycler of claim 14 wherein the switching means is operable selectively to disconnect the supply means from the heating and cooling elements.

17. The thermal cycler of claim 14 wherein the switching means is operable to connect at least some of the heating and cooling elements in series with one another.

18. The thermal cycler of claim 14 wherein the switching means is operable to switch the supply to provide current in a first direction to some of the heating and cooling elements and in a second direction to others of the heating and cooling elements.

19. The thermal cycler of claim 14 wherein the switching means is operable to switch the supply to provide current intermittently to one or more of the heating and cooling elements.

* * * * *

UNITED STATES PATENT AND TRADEMARK OFFICE
CERTIFICATE OF CORRECTION

PATENT NO. : 6,372,486 B1
DATED : April 16, 2002
INVENTOR(S) : David M. Fripp

It is certified that error appears in the above-identified patent and that said Letters Patent is hereby corrected as shown below:

<u>Title page,</u>
Please add: -- Item [30], Foreign Application Data,
    November 30, 1998  GB  9826237.1 --

Signed and Sealed this

Sixth Day of August, 2002

Attest:

Attesting Officer

JAMES E. ROGAN
Director of the United States Patent and Trademark Office

UNITED STATES PATENT AND TRADEMARK OFFICE
CERTIFICATE OF CORRECTION

PATENT NO.   : 6,372,486 B1
DATED        : April 16, 2002
INVENTOR(S)  : David M. Fripp It is certified that error appears in the above-identified patent and that said Letters Patent is hereby corrected as shown below:

<u>Title page, Item [54] and Column 1, line 1,</u>
Title should read -- THERMAL CYCLER --.

Signed and Sealed this

Twenty-fifth Day of February, 2003

JAMES E. ROGAN
*Director of the United States Patent and Trademark Office*